United States Patent [19]

Garcez

[11] Patent Number: 4,753,797

[45] Date of Patent: Jun. 28, 1988

[54] ENHANCING PLATELET MORPHOLOGY PRIOR TO PATIENT USE

[75] Inventor: Randy B. Garcez, Richmond, Calif.

[73] Assignee: Miles Laboratories, Inc., Elkhart, Ill.

[21] Appl. No.: 65,977

[22] Filed: Jun. 24, 1987

[51] Int. Cl.[4] ............................................. A61K 35/14
[52] U.S. Cl. ........................................ 424/101; 435/2
[58] Field of Search ............................ 424/101; 435/2

[56] References Cited

PUBLICATIONS

Han et al—Chem. Abst. vol. 81 (1974), p. 117, 881b.
Ogston et al—Chem. Abst., vol. 94 (1981), p. 100 588g.
Ogston et al., J. Physiol., vol. 310 (1981), pp. 71p–72p.
Han et al., Brit. J. Haematology, vol. 26 (1974), pp. 373–389.

Primary Examiner—Sam Rosen
Attorney, Agent, or Firm—James A. Giblin

[57] ABSTRACT

Platelet morphology in platelet concentrates is significantly enhanced by subjecting the platelets to a gentle heating step. Platelets heated at 37° C. for one hour have at least a 25% increase in the number of disc-like forms over non-heated platelets. When subsequently infused in a patient, the treated platelets show a one hour post-infusion platelet corrected count increment of about 70% higher than non-heated control platelets.

12 Claims, 2 Drawing Sheets

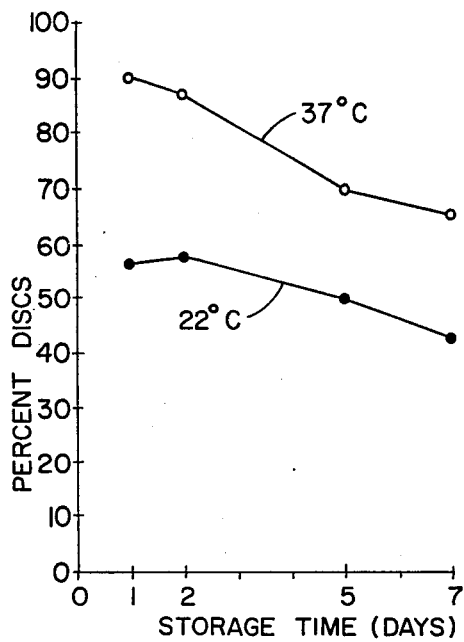
FIG._1.
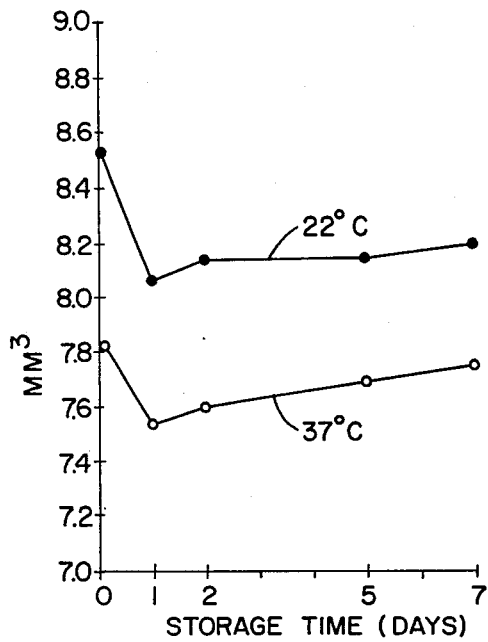
FIG._2.
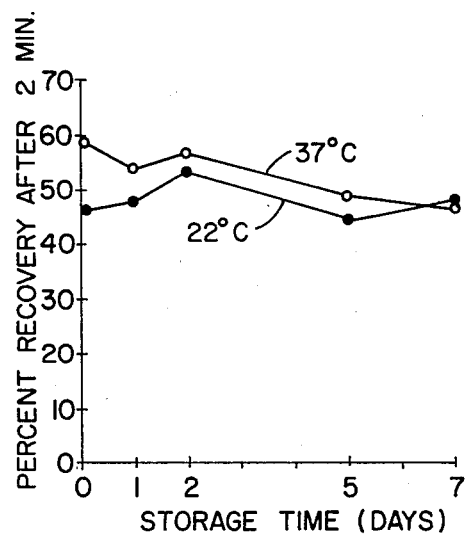
FIG._3.
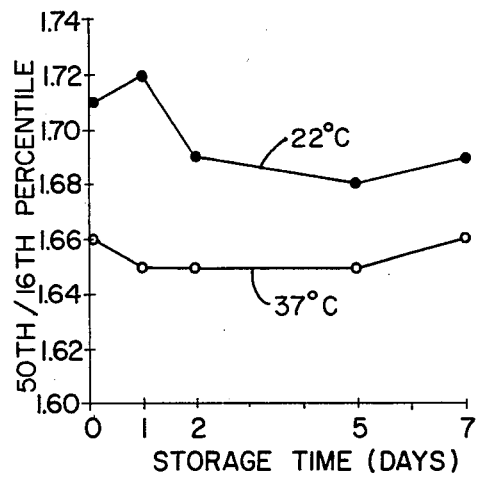
FIG._4.

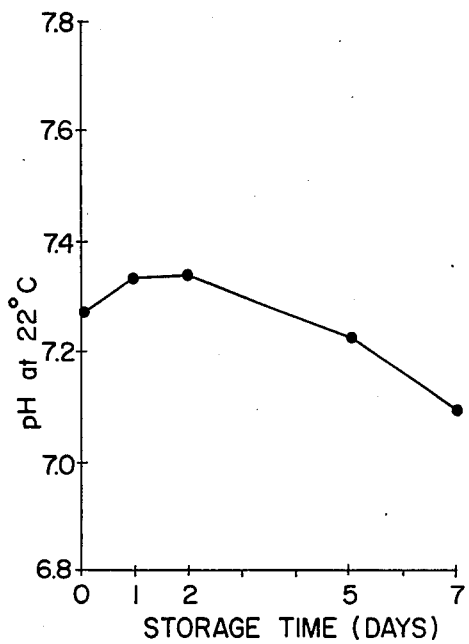
FIG._5.
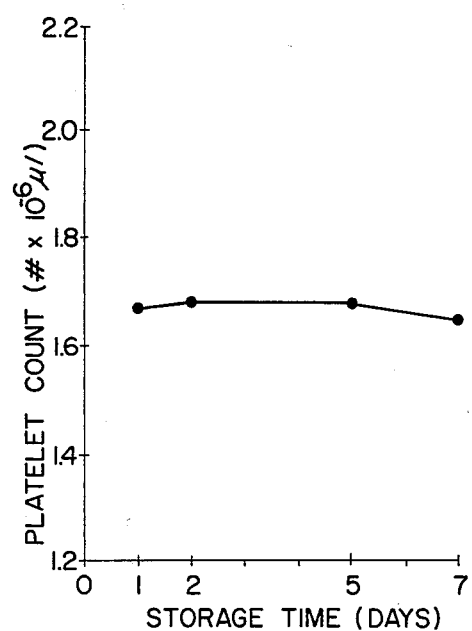
FIG._6.

ENHANCING PLATELET MORPHOLOGY PRIOR TO PATIENT USE

BACKGROUND OF THE INVENTION

Field:

This disclosure is concerned generally with the treatment and storage of platelet preparations. More specifically, the disclosure is concerned with incubating platelets under time and temperature conditions sufficient to enhance the overall morphology and function of the platelets prior to use in treating patients needing platelets.

Prior Art:

Platelets are minute, generally flattened formed bodies found in blood. They are essential to the blood clotting process. Platelets can be easily separated from whole blood via simple centrifugation steps. Platelet concentrates so obtained have been routinely administered to platelet-deficient patients. The infused platelets can be obtained from a single unit of whole blood. More often, however, they are "pooled" with other platelet concentrates to provide sufficient platelet quantity for therapy. The platelets from up to 10 units of blood are commonly pooled to provide a single platelet product suitable for infusion. Such pooling is often accomplished using blood bags especially designed for this purpose and is well known to those skilled in the art.

A preferred platelet pooling system provides for the removal of relatively small amounts of residual white blood cells (WBCs) and red blood cells (RBCs). This allows a platelet-deficient patient on component therapy to receive only that blood component actually needed. In addition, this reduces the likelihood of undesirable febrile reactions that may be attributed to WBCs. A platelet pooling bag capable of removing WBCs and RBCs is disclosed in co-pending patent application Ser. No. 585,793 filed Mar. 2, 1984, in the names of S. Wada et al and assigned to the assignee of this application. See also the bag of similarly assigned Ser. No. 788,993 filed in the name of W. Lewis.

Further information on platelets in general and their storage and use can be found in Platelet Physiology and Transfusion, A Technical Workshop, AABB, 1978. All of the above are incorporated by reference into this disclosure.

It is well known that platelets can be stored at room temperature and this is a common practice. Under such conditions, platelets can be stored for up to 5 to 7 days before infusion. This is especially the case if such storage is in gas permeable blood bags that, by virtue of their $CO_2/O_2$ gas transmissibility feature, help maintain the pH of a platelet preparation at about 6.8 to 7.2. See, for example, U.S. Pat. No. 4,280,497 to R. Carmen et al.

It has long been thought that storage of platelets at elevated temperatures (e.g. significantly above room temperature or at 37° C.) should be avoided. This is due to an expected increase in metabolic activity, leading to greater acid production and pH fall. Earlier studies have consistently indicated that storage at room temperature is generally preferred. Accordingly, except for cases where platelets are inadvertently warmed in transit, they have not been subjected to any particular heating step or heating treatment for any known purpose prior to infusion. In fact, common accepted practice appears to teach away from any prolonged heat treatment of platelets.

I have now found that a controlled heat treatment of platelets at some point prior to infusion results in improved platelet morphology. The results of the heat (incubation) treatment are quite surprising in several respects. Details of these findings are described below.

SUMMARY OF THE INVENTION

The method of enhancing the quality of platelets comprises incubating a separated platelet preparation at elevated temperatures for a period of time sufficient to significantly enhance platelet morphology prior to infusion into a patient. The expression significantly enhanced platelet morphology, as used herein, means an increase of at least 25% in the number of disc-like platelets (discoid platelets) when compared at a given time with non-heated platelets. In preferred embodiments, the separated platelet preparation is initially treated to remove substantially all residual WBCs and RBCs (using, for example, the bags of patent application Ser. Nos. 585,793 and 788,993, cited above). The platelets are then incubated at about 37° C. for at least about 40 minutes, very preferably, for at least about one hour. Ideally, the incubation is in a pH-controlling gas-transmissible plastic platelet bag of the type described in U.S. Pat. No. 4,280,497, and the treated platelets are kept in a relatively "closed" system. This means that, except for platelet pooling techniques, the blood bag system comprises pre-connected sterile bag(s) and tubing(s) which do not permit intrusion from the time whole blood is drawn until the separated and treated platelets are ready for infusion. An added benefit of using the gas-transmissible bag described in the above patent is that the plasticizer used for the PVC film is TOTM, an essentially non-extractable plasticizer.

After the gentle heating treatment of this disclosure, the resulting platelet preparation comprises platelets having about 42–75% of the platelets having a desirable discoid shape. In very preferred embodiments, the treated platelets are also essentially free of residual WBCs and RBCs. The platelets may be infused at about 37° C. or allowed to cool back to room temperature prior to infusion. If allowed to return to room temperature, such heat-treated platelets should be infused into a patient within 3 to 4 hours.

BRIEF DESCRIPTION OF THE FIGURES

FIG. 1 is a graph comparing the % discs of heated and unheated platelets over time.

FIG. 2 is a graph comparing the mean volumes of heated and unheated platelets over time.

FIG. 3 is a graph comparing hypotonic stress over time (as a % platelet recovery after 2 minutes) of heated and non-heated platelets.

FIG. 4 is a graph comparing geometric standard deviation over time of heated and non-heated platelets.

FIGS. 5 and 6 are graphs showing changes in pH and platelet count of platelets stored at room temperature (22° C.) over time.

SPECIFIC EMBODIMENTS

In the Examples below, six units of platelet concentrates (PC), each having a volume of about 60 ml, were tested for the in vitro effects of 37° C. water bath incubation for one hour. Daily aliquots were drawn from each PC and split into 3 groups as detailed in step B for all in vitro tests (other than % Discs). Percent discs was measured on the same PCs before and after the incubation step.

The following procedure was used to make the platelet concentrates.

A. Platelet Concentrate Processing

1. Six units of whole blood were drawn from random donors and centrifuged at 2300 ×g for two minutes and six seconds. The platelet rich plasma (PRP) was removed to one centimeter above the interface. An aliquot of each PRP was drawn for Day 0 tests.

2. Platelet concentrates (PC) were made by centrifuging the PRPs 3750 ×g for six minutes and removing all but sixty ml of the platelet poor supernatant (PPP). The PCs were held at room temperature, unagitated for one hour. The pellets were manually resuspended and stored on an Eberbach shaker at 22° C. throughout the storage period. The PPP was centrifuged at 17,600 ×g to make platelet free plasma (PFP).

In vitro testing was done as follows:

B. In Vitro Testing

1. Day 0-Testing was conducted as follows:
    The PRP from step A.1 was tested at room temperature of 22° C. (RT) for pH, platelet count and sizing. The PRP samples were diluted with PFP to a count of 250,000/μL. The diluted samples were split into three portions with their residual air purged with 5% $CO_2$ : 20 % $O_2$ : 75% $n_2$ air and the following tests were done:
    a. one hour at RT—Hypotonic stress
    b. one hour at 37° C.—Hypotonic stress
    c. one hour at 37° C.—Platelet sizing 2. Day 1, 2, 5 and 7
    Samples of each PC were drawn and pH, sizing and count assays were performed. Each PC was diluted with PFP to a count of 250,000/μL. Diluted samples were then split into three aliquots with their residual air purged with 5% $CO_2$ : 75% $N_2$ air. The following tests were done:
    a. one hour at RT—Hypotonic stress
    b. one hour at 37° C.—Hypotonic stress
    c. one hour at 37° C.—Platelet sizing
    Each PC was also tested for RT % discs using the test described below and placed in a plastic pouch which was suspended upright in a 37° C. water bath for one hour and tested again for % discs by the same test.

Individual and combined results are shown in FIGS. 1-6. The following comparisons show in greater detail what occurred in the platelets and PC incubated at 37° C. for about 1 hour versus platelets and PC incubated at 22° C. for the same period.

1. % Discs
    37° C. PC had an average increase of 50.0 ±7.1% in the number of discs on all days. See FIG. 1.
2. Geometric Standard Deviation (GSD)
    GSD (a measure of size dispersion) lowered from an average value of 1.70 (22° C.) to 1.65 (37° C.) on all days (p <0.01). See FIG. 4.
3. Mean Volume
    The mean platelet volume decreased from an average value of 8.22 ±0.18 $\mu M^3$ (22° C.) to 7.69±0.11 $\mu M^3$ (37° C.) on all days (p <0.01). See FIG. 2.
4. Hypotonic Stress
    The % recovery in 37° C. incubated PC was significantly higher (p <0.05) in the platelet rich plasma (PRP) and PC at Days 1 and 2. Stress recoveries for these points were higher by 28.4%, 17.0% and 7.6% respectively. There were no differences in the Day 5 and 7 samples. See FIG. 3.
5. pH, Count
    pH and platelet count were both stable throughout the storage and testing procedures. All room temperature data exhibited no difference compared to historical data. See FIG. 5.

In the examples of this disclosure, percent discs was measured by the Non-Invasive Assessment of Platelet Shape and Concentration (NAPSAC) machine, described in more detail in U.S. Pat. No. 4,522,494 to R. F. Bonner and available from Beecher Medical, Silver Spring, Md. Measurements were made at room temperature (RT/22° C.) and again after the 37° C. incubation period. (The results in Tables 1 and 2 below are from field studies of individual and pooled PCs from local blood banks).

TABLE 1

| | % Discs Individual PC (single donor) | | | | |
|---|---|---|---|---|---|
| PC | Days Stored at 22° C. | | | | |
| Temperature | 1 | 2 | 3 | 4 | 5 |
| 22° C. | 56.9 ± 17.1 | 36.4 ± 14.7 | 43.0 ± 18.5 | 39.1 ± 10.3 | 34.5 ± 20.4 |
| 37° C. | 75.2 ± 17.6 | 55.9 ± 23.0 | 59.7 ± 10.0 | 51.9 ± 17.2 | 42.4 ± 24.9 |
| Difference | 18.0 ± 9.4 | 19.6 ± 14.4 | 15.8 ± 10.0 | 14.6 ± 8.7 | 8.4 ± 8.2 |
| n | 13 | 16 | 16 | 16 | 20 |

TABLE 2

| | % Discs Pooled PC (6 PC/pool) |
|---|---|
| PC Temperature | Pool (n = 9) |
| 22° C. | 39.0 ± 14.3 |
| 37° C. | 58.4 ± 13.0 |
| Difference | 19.4 ± 8.6 |

Table 1 shows the increases in % discs (P <0.001) caused by incubation (1 hour at 37° C.) for PC stored from 1 to 5 days at RT. This increase was much less on day 5 versus all other storage days. Pooled PC (Table 2) performed as well or better than individual PC. This study shows dramatic improvements in platelet morphology (significantly enhanced platelet morphology) due to the incubation. Since good platelet morphology has been associated with good in vivo scores, this incubation step prior to transfusion is thought to improve in vivo viability. See preliminary in vivo results, summarized below.

In addition to the significantly enhanced platelet morphology caused by the incubation, such platelets will decrease in mean volume by about 0.5 $\mu m^3$ when stored at 22° C. for up to 7 days. As pointed out above, such PC will also have at least 25% (preferably at least 50%) more disc-like platelets than PCs that have not been incubated in accordance with this disclosure.

C. In Vivo Testing:

Preliminary clinical studies (N=4) show mean post-transfusion platelet corrected count increments (CCI) at one and two hours to be 68.6% and 44.4% higher, respectively for platelet transfusions that had been heat treated for 1 hour at 37° C. (compared to non-heat treated or RT platelets).

DISCUSSION

PC transfusions are currently carried out at room temperature (about 22° C.) to a patient whose body temperature is about 37° C..

The above studies show that many platelet in vitro parameters change during the first hour of temperature change. Platelet size and dispersion becomes smaller, more discs appear, and higher hypotonic stress recoveries (up to Day 2 storage) occur. These changes stabilize after about one hour at the higher temperature.

In view of the above in vitro and preliminary in vivo studies, it is thought that platelets equilibrated to body temperature for one hour prior to transfusion could possibly result in increased in vivo recovery of the platelets transfused. This is based on the following possibilities:

1. Pseudopod Retraction/Size
   Decreased pseudopododia might lower the chance of removal by the reticuloendothelial system (RES). Less surface exposure due to smaller size might decrease possible stimulation and activation of platelets immediately following transfusion.
2. Increased Disc Formation
   Normal platelet morphology is discoid. Disc to sphere formation is a common first reaction to most stimuli. A reversal of sphere to disc formation would indicate a normalization of the platelets. Good in vivo results have always occurred with PC having good morphology. See S. Murphy et al, Platelet Storage for Transfusion, Seminars in Hematology, Vol. 22, No. 3, pp. 165-177, (1985).
3. Hypotonic Stress Recovery (HSR)
   HSR has a fair correlation to in vivo recoveries. See, C. R. Valeri et al, "The relation between response to hypotonic stress platelets", Transfusion 14:331 (1974). Modest increases in HSR scores occurred through Day 2 of storage.

Conclusion

The platelets incubated at elevated temperatures such as 37° C. for a prolonged period (at least 40 minutes to an hour) were stabilized and exhibited many in vitro benefits with no adverse effects on further storage on the PC. Preliminary in vivo tests show that PCs heated for 1 hour at 37° C. prior to infusion show a post-infusion CCI of about 70% (68.2%, N=4) higher one hour after transfusion and a CCI of about 45% (44.4%, N=4) higher two hours after infusion, when compared with non-heated platelets, respectively.

Given this disclosure, it is thought that variations in the incubation method will occur to those skilled in the art. Accordingly, it is intended that the above examples should be construed as illustrative and that the scope of the invention disclosed here should be limited only by the following claims.

I claim:

1. A method of treeating platelets in a platelet concentrate preparation, the method comprising incubating the preparation prior to infusion into a patient at elevated temperatures for a period of time sufficient to result in an increase of at least 25% in the number of discoid platelets when compared with non-incubated platelets at a given time of platelet storage.

2. The method of claim 1 wherein the increase is at least about 50%.

3. The method of claim 1 wherein the incubation is at a temperature of about 37 ° C.

4. The method of claim 1 wherein the incubation is for at least about 40 minutes.

5. The method of claim 1 wherein the incubation is at 37 ° C. for least about one hour.

6. In a method of preparing a platelet concentrate suitable for infusion into a patient and comprising the steps of
   (a) collecting whole blood from a donor and separating the blood into a red blood cell component and a platelet rich plasma component;
   (b) separating platelets from the platelet rich plasma component;
   the improvement comprising incubating the separated platelets at about 37 ° C. for at least about 40 minutes under conditions sufficient to increase the number of discoid platelets by at least 25% when compared with non-incubated platelets at a given time in platelet storage.

7. The method of claim 6 wherein the increase is at least 50%.

8. The method of claim 6 wherein prior to the incubation step, substantially all residual WBCs and RBCs are removed from the platelets.

9. A platelet concentrate comprising at least about 65% platelets having a disc-like shape after 7 days storage at room temperature.

10. The platelet concentrate of claim 9 in a platelet pooling bag.

11. The platelet concentrate of claim 9 in a gas-transmissible plastic bag.

12. The platelet concentrate of claim 9 wherein the bag is made from a plastic film comprising polyvinylchloride plasticized with trioctyltrimellitate plasticizer.

* * * * *